(12) United States Patent
McAdam et al.

(10) Patent No.: US 11,612,474 B2
(45) Date of Patent: Mar. 28, 2023

(54) PACKAGING FOR MEDICAL DEVICE

(71) Applicant: C.R. Bard, Inc., Murray Hill, NJ (US)

(72) Inventors: James McAdam, Coventry, RI (US); Pam Fotopoulos, Foster, RI (US); Timothy Early, Winona Lake, IN (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 17/852,465

(22) Filed: Jun. 29, 2022

(65) Prior Publication Data

US 2022/0323193 A1    Oct. 13, 2022

Related U.S. Application Data

(63) Continuation of application No. 16/768,045, filed as application No. PCT/US2018/063010 on Nov. 29, 2018, now Pat. No. 11,406,484.

(60) Provisional application No. 62/592,026, filed on Nov. 29, 2017.

(51) Int. Cl.
*A61F 2/00* (2006.01)
*B65D 77/04* (2006.01)

(52) U.S. Cl.
CPC .......... *A61F 2/0095* (2013.01); *A61F 2/0063* (2013.01); *B65D 77/04* (2013.01)

(58) Field of Classification Search
CPC ..... A61F 2/0095; A61F 2/0063; B65D 77/04; A61B 50/30
USPC ....................................................... 206/438
See application file for complete search history.

(56) References Cited

U.S. PATENT DOCUMENTS

| 5,249,682 A | 10/1993 | Transue |
| 5,972,008 A | 10/1999 | Kalinski et al. |
| 7,481,314 B2 | 1/2009 | Komarnycky |
| 8,292,076 B2 | 10/2012 | Dacey |
| 8,517,174 B2 | 8/2013 | Dacey et al. |
| 8,567,162 B2 | 10/2013 | Bagga et al. |
| 11,406,484 B2 * | 8/2022 | McAdam .............. A61F 2/0095 |
| 2011/0226762 A1 | 9/2011 | Mermet |
| 2011/0308983 A1 | 12/2011 | Dacey et al. |
| 2014/0005471 A1 | 1/2014 | Amarasinghe et al. |

(Continued)

FOREIGN PATENT DOCUMENTS

| CN | 101687053 A | 3/2010 |
| EP | 0 625 334 A1 | 11/1994 |

(Continued)

OTHER PUBLICATIONS

International Search Report and Written Opinion for International Application No. PCT/US2018/063010, dated Mar. 18, 2019.

(Continued)

*Primary Examiner* — Jacob K Ackun
(74) *Attorney, Agent, or Firm* — Wolf, Greenfield & Sacks, P.C.

(57) ABSTRACT

Packaging for a medical implant such as a hernia repair prosthetic material includes a carrier and a stiffener. The hernia repair prosthetic material is placed adjacent to the stiffener within the carrier. The carrier assembly is sealed within an outer pouch, such as a foil pouch, and sterilized. When the carrier is being removed from the pouch in preparation for surgery, the stiffener helps prevent the carrier assembly from contacting non-sterile portions of the pouch.

11 Claims, 10 Drawing Sheets

(56) References Cited

U.S. PATENT DOCUMENTS

| | | |
|---|---|---|
| 2014/0090999 A1 | 4/2014 | Kirsch et al. |
| 2015/0209129 A1 | 7/2015 | Bailly et al. |
| 2016/0310253 A1 | 10/2016 | Ferrand et al. |
| 2016/0310254 A1 | 10/2016 | Ferrand et al. |
| 2019/0209282 A1 | 7/2019 | Griffiths et al. |

FOREIGN PATENT DOCUMENTS

| | | |
|---|---|---|
| FR | 2710518 A1 | 4/1995 |
| FR | 2 873 567 A1 | 2/2006 |
| JP | 2011/522745 A | 8/2011 |
| WO | WO 2014/049446 A2 | 4/2014 |

OTHER PUBLICATIONS

International Preliminary Report on Patentability for International Application No. PCT/US2018/063010, dated Jun. 2, 2020.

* cited by examiner

PACKAGING FOR MEDICAL DEVICE

RELATED APPLICATIONS

This Application is a Continuation of U.S. application Ser. No. 16/768,045, filed May 28, 2020, entitled "PACKAGING FOR MEDICAL DEVICE", which is a national stage filing under 35 U.S.C. 371 of International Patent Application Serial No. PCT/US2018/063010, filed Nov. 29, 2018, entitled "PACKAGING FOR MEDICAL DEVICE", which claims the benefit of U.S. Application Ser. No. 62/592,026, filed Nov. 29, 2017, entitled "PACKAGING FOR MEDICAL DEVICE" hereby incorporated herein by reference in its entirety.

FIELD

The disclosure is directed generally to packaging for a medical device, and more specifically to packaging that facilitates removal of a sterilized medical implant from a pouch.

DISCUSSION OF THE RELATED ART

One approach to repairing a hernia is to cover the tissue or muscle wall defect with a patch of repair prosthetic material, such as a fabric mesh. Prior to storage and transport, a hernia repair prosthetic material is placed into a foil pouch which is then sealed and then sterilized. Typically, during the sterilization process, prior to placing the prosthetic material into the pouch, the hernia repair prosthetic material is secured in a carrier, such as a flexible envelope made of High Density Polyethylene (e.g., Tyvek® brand HDPE material).

SUMMARY

According to one aspect, a surgical material assembly includes a flat, flexible carrier including a first surface and an opposed second surface. The flat hernia repair prosthetic material is held within the carrier between the first and second surfaces, and the flat hernia repair prosthetic material has a first side and a second side. A stiffener is positioned within the carrier adjacent to the flat hernia repair prosthetic material, the stiffener being positioned on only the first side of the hernia repair prosthetic material, and the stiffener being stiffer than the carrier in resisting out of plane bending.

According to another aspect, a surgical material assembly includes a flat, flexible carrier having a first end and a second end, and a flat hernia repair prosthetic material held within the carrier. A stiffener is positioned within the carrier adjacent to the flat hernia repair prosthetic material, the stiffener having a first end located near the carrier first end, and a second end located near carrier second end. The assembly includes a handle attached to the stiffener at the stiffener first end, with the handle protruding beyond the carrier first end when the carrier is closed.

According to a further aspect, a surgical material assembly includes a flat, flexible carrier, and a flat hernia repair prosthetic material held within the carrier. The assembly includes a flat stiffener positioned within the carrier, with the stiffener and having a flat surface on which the hernia repair prosthetic material is positioned, and the stiffener being stiffer than the carrier in resisting out of plane bending. When the carrier is opened and the hernia repair prosthetic material is not restricted by the carrier, the stiffener does not prevent movement of the hernia repair prosthetic material across the flat surface of the stiffener.

According to another aspect, a method of sterilizing a hernia repair prosthetic material and a flat, flexible carrier holding the prosthetic material is provided. The method includes placing a stiffener on a first surface of the flat flexible carrier, the stiffener having a handle, and placing the hernia repair prosthetic material on the stiffener. The method further includes securing the flat flexible carrier to the stiffener and hernia repair prosthetic material such that the handle protrudes beyond an end of the carrier, placing the carrier into a pouch, and sealing the pouch. Finally, the method includes sterilizing the pouch, carrier, stiffener, and hernia repair prosthetic material.

BRIEF DESCRIPTION OF DRAWINGS

Aspects of the invention are described below, by way of example, with reference to the accompanying drawings in which like numerals reference like elements, and wherein.

DETAILED DESCRIPTION

Figure 1:
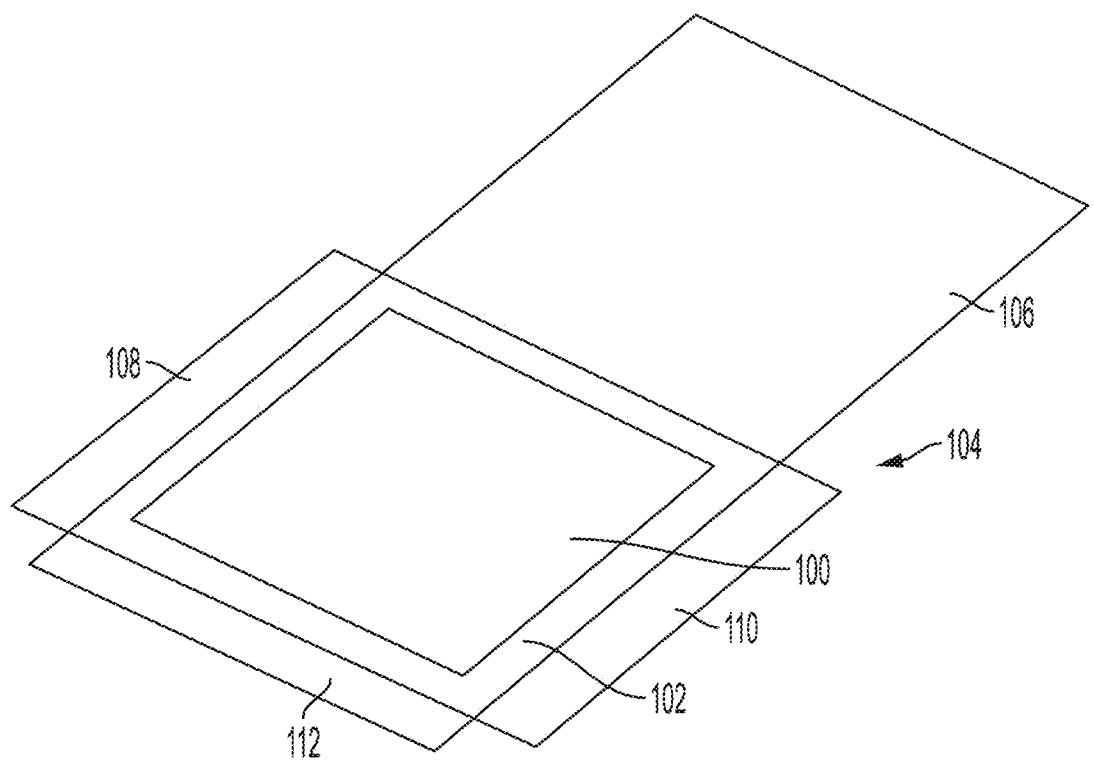
FIG. 1 shows an open, flat, flexible carrier with a hernia repair prosthetic material placed on a first panel of the carrier.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with packaging for handling hernia repair prosthetic material, such as implantable mesh material, but the invention is not necessarily so limited, and may be used with other materials that require storage and handling, including other types of medical implants and surgical tools.

For storage and handling, hernia repair prosthetic material is often held in a flat carrier made of thin, flexible high density polyethylene (HDPE) and then placed in a foil pouch which is then sealed. The pouch, carrier, and prosthetic material are sterilized, often with ethylene oxide gas. To retrieve the prosthetic material for surgery, a non-sterile user opens the foil pouch by pulling on flaps at the upper end of the pouch to peel the pouch's two sealed panels apart from each other. A sterile user removes the carrier from the foil pouch by grasping the carrier and pulling the carrier through the opened end of the foil pouch.

Applicants have discovered that when a large prosthetic material and its carrier are removed from the foil pouch, the carrier can touch inner-facing surfaces of the flaps that the non-sterile user uses to pull apart the foil pouch. These inner-facing surfaces are non-sterile, and as a result, the exterior of the carrier may become contaminated if care is not taken when removing the carrier from the pouch.

According to one aspect of the present disclosure, a stiffener is provided with the carrier and prosthetic material to facilitate avoiding contact between the carrier and the foil pouch. In some embodiments, the stiffener includes a handle which further eases removal of the carrier from pouch.

The stiffener may be constructed and arranged to limit out of plane bending through its materials of construction and/or geometry. For example, the stiffener may be a flat, rectangular sheet of HDPE with sufficient thickness to prevent significant out of plane bending of the sheet and thus the carrier when the sheet is supported at one end. In other embodiments, the stiffener may have a rectangular ring shape, an X-shape, an I-shape, a T-shape, or any other suitable shape.

The handle may be integral with the stiffener in some embodiments, or the handle may be a non-integral component which is attached to the stiffener. Some embodiments include no handle, and the sterile user grasps the outer surface of the carrier rather than a handle of the stiffener. In still further embodiments, the carrier may include a handle, such as a looped extension of a flexible material.

Figure 2:
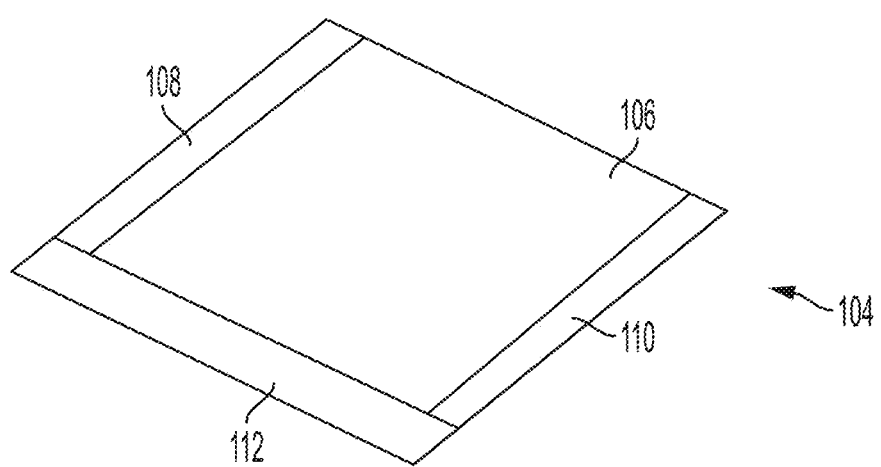
FIG. 2 shows the flexible carrier of FIG. 1 in a closed configuration.

Turning to the figures, FIG. 1 shows a prosthetic mesh 100 placed on a first panel 102 of a flexible carrier 104. A second panel 106 is foldably attached to first panel 102, and edge pieces 108, 110 and an end piece 112 on the first panel are attachable to the second panel 106 such that carrier 104 can hold the prosthetic material. FIG. 2 shows flexible carrier 104 closed around the prosthetic material with the edge pieces 108, 110 and the end piece 112 folded over the first panel. The flexible carrier may be made of a synthetic material such as a flexible HDPE. Tyvek® brand HDPE may be used in some embodiments, as may medical grade papers.

Figure 3:
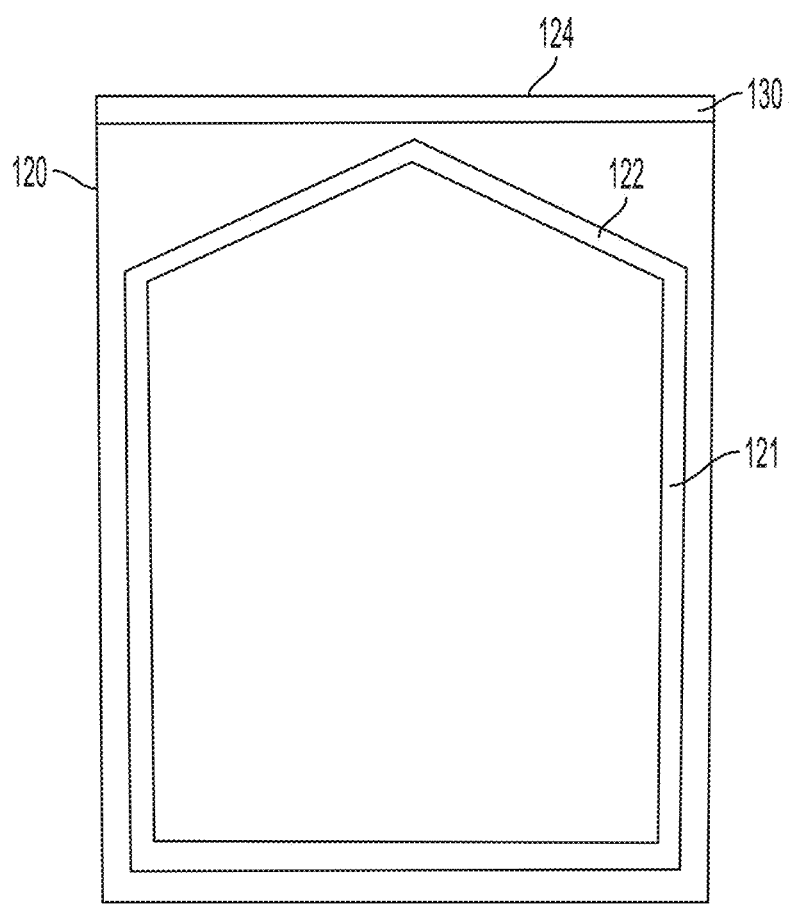
FIG. 3 shows a foil pouch used to hold a sterile hernia repair prosthetic material.

The assembly of the prosthetic material and the carrier is sterilized, typically with ethylene oxide. After sterilization, the carrier and prosthetic material are dehumidified and placed in a moisture-impervious pouch, such as a foil pouch 120 shown in FIG. 3. After the sterilized carrier assembly has been placed in foil pouch 120, the pouch is sealed, for example via heat sealing.

Figure 4:
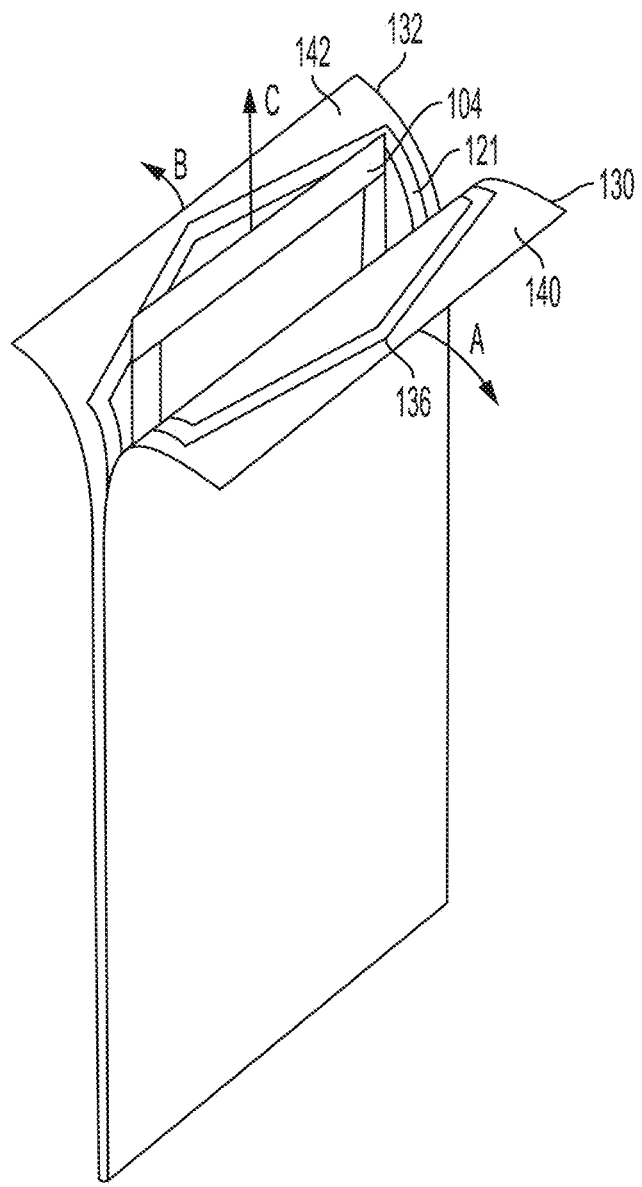
FIG. 4 shows the foil pouch of FIG. 1 being opened to allow removal of a flexible carrier holding hernia repair prosthetic material.

Foil pouch 120 includes a heat seal 121 having a chevron shape 122 at a first end 124 of the pouch in the illustrated embodiment. The first end 124 is the end which is opened to access the carrier and prosthetic material. To open the pouch, the user grasps first and second flaps 130, 132 (see FIG. 4) and pulls them apart from one another (see Arrows A and B). The forces on the flaps separate the seal starting at a tip 136 of the chevron-shaped portion of the seal. The user then pulls the carrier 104 out of the foil pouch in the direction of arrow C.

As mentioned above. Applicant has discovered that with certain sizes of carriers and/or prosthetic materials, as the flexible carrier 104 is pulled from the pouch, the flexible carrier may contact first and second interior surfaces 140, 142 of first and second flaps 130, 132 through sagging or bending. Because these surfaces of the carrier are outside of the heat seal, they are not considered sterile, and therefore may contaminate an exterior of the carrier.

Figure 5:
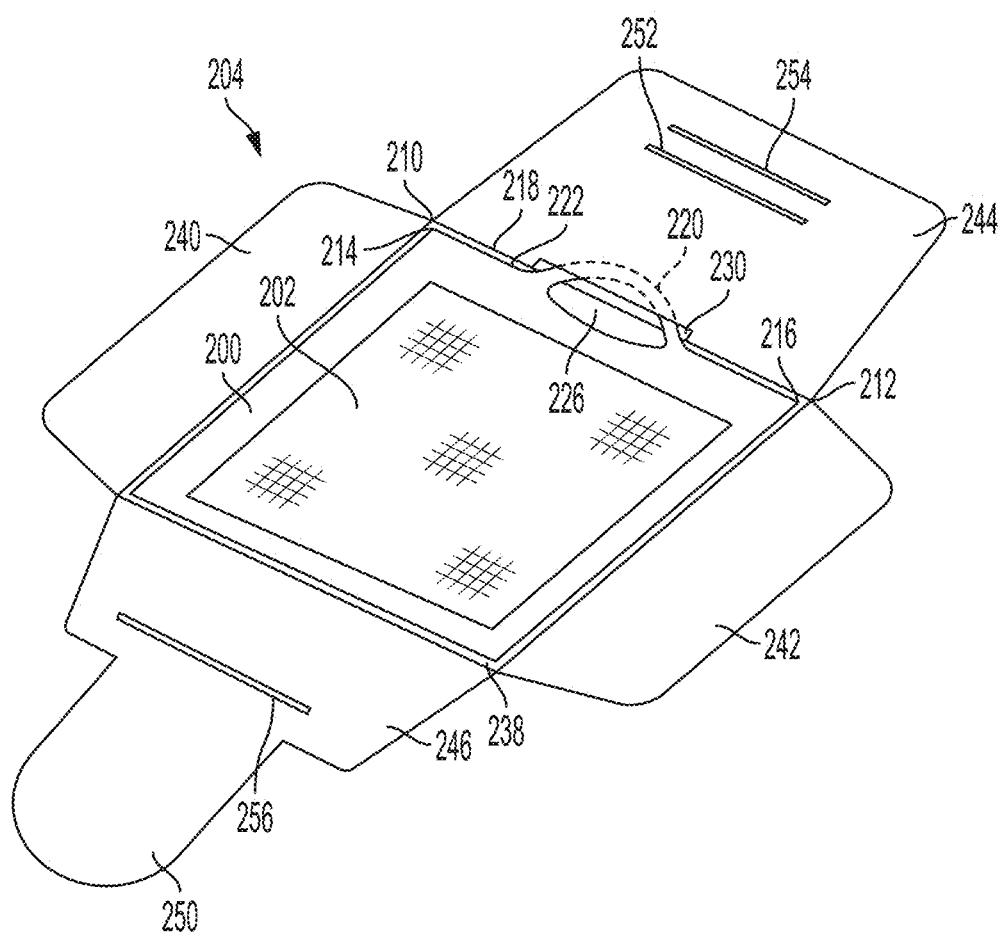
FIG. 5 shows an open flexible carrier with a stiffener and a hernia repair prosthetic material placed on the stiffener according to one embodiment of the disclosure.

FIG. 5 shows one embodiment of a package assembly configured to help prevent such non-sterile contact. A flexible carrier 204 includes a stiffener 200 configured to limit out of plane bending of the carrier 204. A hernia repair prosthetic material 202 is shown placed on top of stiffener 200. In the illustrated embodiment, the stiffener is longer and wider than the prosthetic material 202. The stiffener may have a size and/or shape that is similar to the prosthetic material in some embodiments, though in other embodiments, the stiffener may have a different size and/or shape. Similarly, the stiffener may have a size and/or shape that is similar to a panel of the carrier 204, or, the stiffener may be a different size and/or shape.

The stiffener may be sized and shaped to extend within a specified distance of first and second upper corners 210, 212 of carrier 204. For example, a first upper corner 214 of stiffener 200 may reach within three centimeters of first upper corner 210, and a second upper corner 216 of stiffener 200 may reach within three centimeters of second upper corner 212 in some embodiments. In other embodiments, the stiffener corners may extend to within one centimeter of the carrier corners.

By reaching close to the corners of the carrier, the stiffener can help prevent the corners and edges of the carrier from sagging or bending toward the interior surfaces of the pouch flaps. Additionally, by providing a stiffer surface for the user to grasp, the user may use one hand to remove the carrier instead of two hands in some embodiments. Using one hand may reduce the chances of inadvertently bumping the flaps and moving the flaps into contact with the carrier.

The stiffener may be sized to reach lower corners of the carrier as well. For example, in some embodiments, the lower corners of the stiffeners may be positioned within three centimeters or less, or one centimeter or less of the lower corners of the carrier, or any other suitable distance.

Stiffener 200 may be made of a sheet of HDPE (such as Tyvek® brand HDPE) having a greater thickness than the carrier material. For example, in some embodiments, the stiffener may have a thickness of at least one millimeter, for example, one millimeter or 1.5 millimeters. Other embodiments may include a stiffener with a thickness of two millimeters or more. Smaller thickness, such as 0.5 millimeters, may be used in some embodiments. HDPE is a hydrophobic material, and other hydrophobic materials may be used to form the stiffener. A hydrophilic material may be added to the stiffener if desired in some embodiments, or the stiffener itself may include a hydrophilic material. In some embodiments, the stiffener is at least as hydrophobic as the carrier.

The stiffener may be sized and shaped to extend within a specified distance of an upper end of the carrier, such as upper edge 218. For example, the stiffener may reach to within five centimeters of the carrier upper end. That is, the upper edge of the stiffener may be five centimeters or closer to the carrier upper end. In some embodiments, the upper edge of stiffener may be three centimeters or closer to the upper end of the carrier. In still other embodiments, the stiffener upper edge may be a half centimeter (or closer) from the upper end. The stiffener may be the same length as the interior of the carrier in some embodiments such that the upper and lower ends of the stiffener contact the interior folded edges of the carrier. In still further embodiments, the stiffener may be longer than the interior of the carrier such that closing the carrier necessarily forces the stiffener ends into contact with the upper and lower interior edges of the carrier.

Similarly, the stiffener width may be sized to be five centimeters or closer to the carrier side edges, three centimeters or closer, or a half centimeter or closer. In some embodiments, the stiffener may be as wide as the interior width of the carrier, or wider than the interior width of the carrier.

A handle may be provided as part of the stiffener according to one aspect of the present disclosure. For example, a handle 220 may be integrally formed with the stiffener and located at a lateral center of an upper edge 222 of the stiffener. In some embodiments, the handle may be separately formed and attached to the stiffener. The stiffener may include two or more handles in other embodiments. The handle shown in the illustrated embodiment includes an arch that extends away from the upper edge 222 of the stiffener and an opening 226 that extends below the upper edge of the stiffener. Other handle arrangements may be used.

As visible in FIG. 5, carrier 204 may include a slot opening 230 positioned in or near its upper edge 218 such that handle 220 extends through the opening 230 and is accessible for grasping by a user when the carrier is in a closed configuration. This arrangement may permit a user to easily remove the carrier from the foil pouch and/or carry the carrier to a suitable location after removal.

Hernia repair prosthetic materials are typically flexible and come in various sizes and shapes. In some cases, a prosthetic mesh can be on the order of 50 centimeters long and 50 centimeters wide. According to some embodiments disclosed herein, a stiffener may be sized to be wider and/or longer than the hernia repair prosthetic material that is packaged with the stiffener. In other embodiments, the stiffener may be the same size as the hernia repair prosthetic material, or have one dimension (e.g., length or width) that is the same size or smaller as the prosthetic material. In some embodiments, the stiffener may be smaller in all dimensions that the prosthetic material.

Other than the handle, the stiffener illustrated in FIG. 5 does not include any openings, slots, or other components. As a result, the stiffener does not have components which restrict movement of the prosthetic material. With such an arrangement, when the carrier is laid flat and opened, the prosthetic material is easily picked up from above. In other embodiments, tabs, slots, and/or other components may be used to secure the prosthetic material to the stiffener or prevent movement of the prosthetic material in one or more directions.

As shown, the stiffener is adjacent to only one side of the prosthetic material in some embodiments. By having a non-folded stiffener that does not sandwich the prosthetic material and contact both a first side and a second side of the prosthetic material, the overall thickness of the packaging is limited in some embodiments. Additionally, when the carrier is in an open configuration, the non-folded stiffener may allow the prosthetic material to be removed from the stiffener in a direction that is transverse to the flat surface of the stiffener.

In other embodiments, the stiffener may fold over the prosthetic material, or have components that fold over the prosthetic material. In some embodiments, an additional component may be positioned between the stiffener and the prosthetic material, in which case the stiffener is adjacent to only one side of the prosthetic material but is not in direct contact with the prosthetic material.

Figure 6:
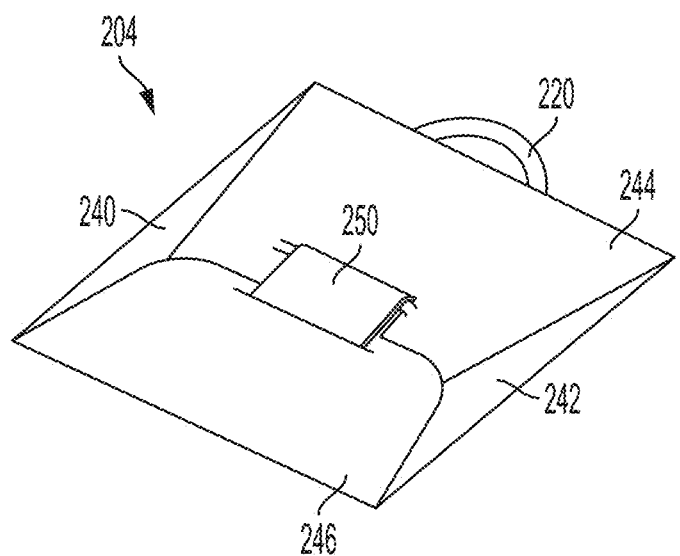
FIG. 6 shows an assembly of the carrier, stiffener, and hernia repair prosthetic material of FIG. 5 with the carrier in closed configuration, according to one embodiment of the disclosure.

The flexible carrier includes one side formed of a full panel, and a second side formed with flaps extending from the first panel in some embodiments. For example, flexible carrier 204 includes a first panel 238 with foldably attached first and second side flaps 240, 242, an upper end flap 244, and a lower end flap 246. Once the stiffener 200 and prosthetic material 202 have been placed on the inside of first panel 238, side flaps 240, 242 are folded over the prosthetic material and stiffener. Next, upper end flap 244 is folded over the side flaps, and lower end flap 246 is folded over upper end flap 244. According to the illustrated embodiment, a tab 250, which extends from the lower end flap 246, is passed through two slots 252, 254 in the upper end flap. The tab is folded over itself and inserted into a slot 256 in the lower end flap. Carrier 204 is shown in a closed configuration in FIG. 6. Other arrangements for opening and closing the carrier may be used. For example, the carrier shown in FIG. 1 may be used in some embodiments.

In some embodiments, the carrier may include a pocket which removably holds the stiffener within the carrier. For example, a stiffener pocket may extend partway from a lower end of first panel 238 toward the top end and have an opening facing the upper edge of the first panel. In other embodiments, a stiffener may be permanently attached to a carrier, for example in an enclosed pocket or by an adhesive.

Figure 7:
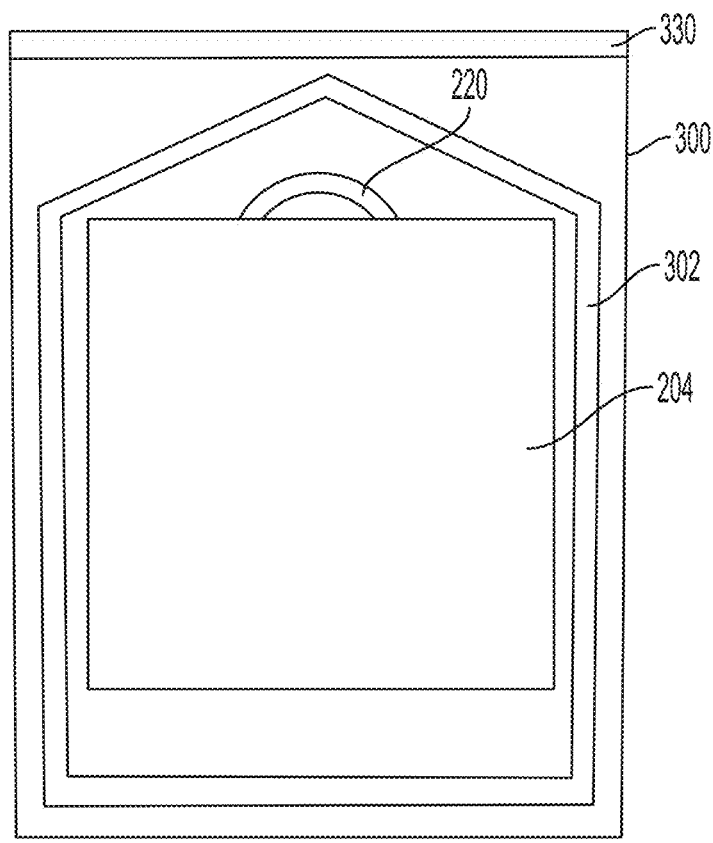
FIG. 7 shows the assembly of FIG. 6 enclosed within a sealed pouch according to one embodiment of the disclosure.

FIG. 7 shows one possible configuration of the carrier of the present disclosure within a foil pouch 300 have a perimeter seal 302. For ease of illustration, the pouch is shown as transparent, but an opaque material such as foil may be used. In the illustrated embodiment, the stiffener is larger than the prosthetic material in both width and length, and handle 220 is positioned within the chevron-shaped portion of the perimeter seal 302. In this manner, the foil pouch size is not increased relative to a pouch which holds a carrier that lacks a stiffener. Additionally, the handle is presented to the user close to the upper end of the pouch when the foil pouch is peeled open.

Perimeter seal 302 may be a heat seal, a pressure seal, an adhesive seal, or any other suitable seal.

Figure 8:
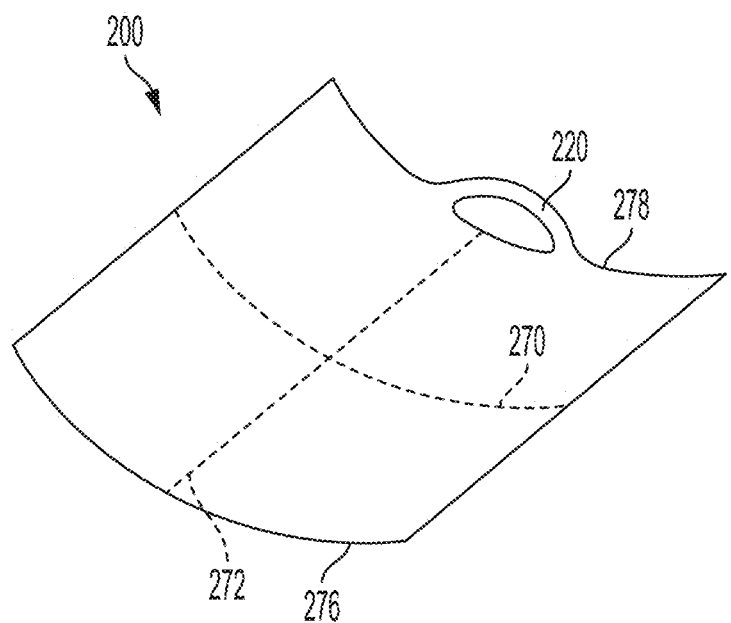
FIG. 8 shows a stiffener transversely bent out of plane according to one embodiment of the disclosure.

FIG. 8 shows stiffener 200 bent in the transverse direction such that its transverse axis 270 has a positive curvature (an upward curve). In some embodiments, the stiffener may be transversely bent to improve the stiffener's resistance to bending outwardly along its longitudinal axis 272. For example, when supporting the stiffener at an upper end 278, a positive transverse curvature may reduce the amount of deflection of a lower end 276. When the carrier and stiffener are being removed from a pouch at an angle relative to vertical (e.g., 45° or horizontally), this positive transverse curvature may help prevent the lower portions of the carrier from bending and contacting the inside surfaces of the foil flaps.

Figure 9:
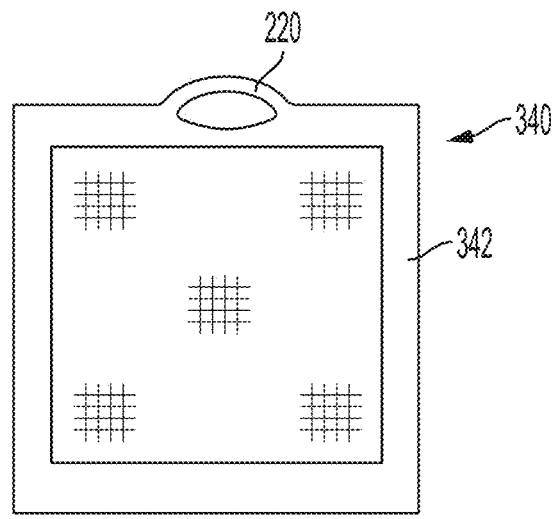
FIG. 9 shows a stiffener with a rectangular ring shape.
Figure 10:
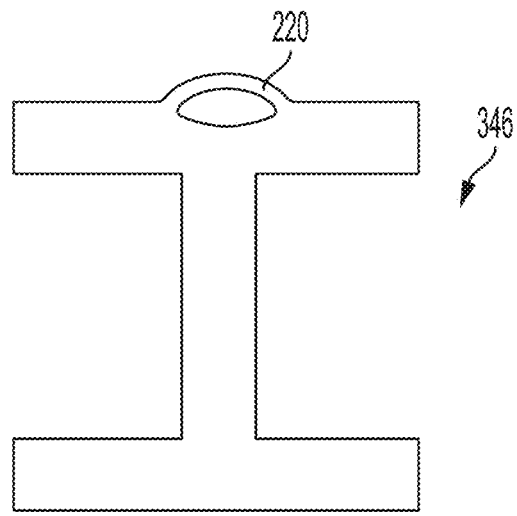
FIG. 10 shows a stiffener with an I-shape.
Figure 11:
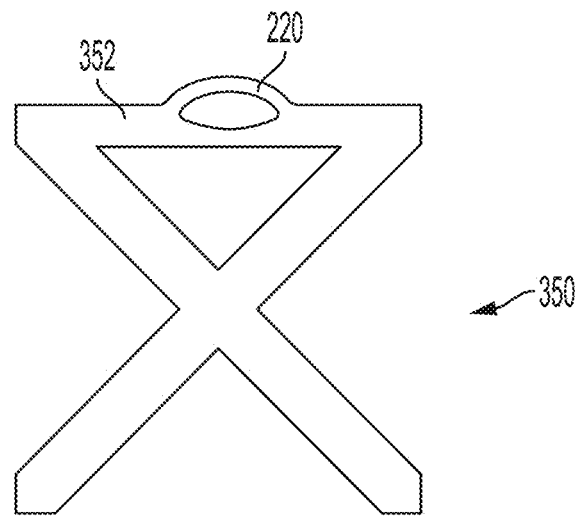
FIG. 11 shows a stiffener with an X-shape.
Figure 12:
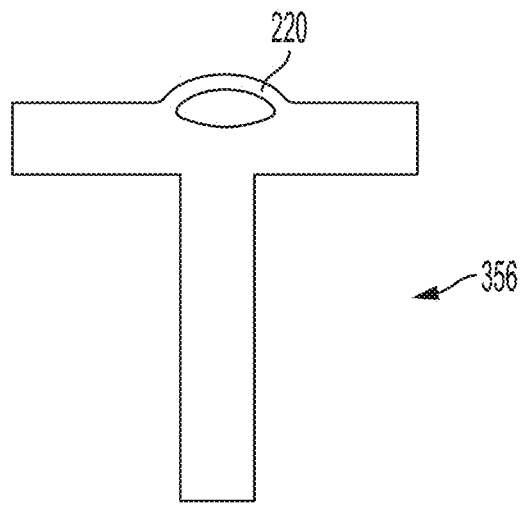
FIG. 12 shows a stiffener with a T-shape.

FIG. 9 shows an alternative embodiment where a rectangular stiffener 340 is formed with a rectangular ring 342. Other ring shapes may be used, for example, an oval ring, a circular ring, a triangular ring, or any other suitable ring shape. FIG. 10 shows an I-shaped stiffener 346. FIG. 11 shows an X-shaped stiffener 350 with a transverse section 352 to which handle 220 is attached. FIG. 12 illustrates a T-shaped stiffener 356. Rectangular sheets of prosthetic material (or other shapes) may be supported by the stiffeners shown in FIGS. 9-12 even though the stiffener and the prosthetic material sheet would not have the same shape. The prosthetic material may slightly bend or sag in the areas that are not adjacent to the stiffener, but the stiffener may be configured to permit an amount of bending that does not typically allow the prosthetic material to reach the interior surface of the pouch flaps.

In each of the embodiments shown in FIGS. 10-12, the stiffener has a varying width along the stiffener length. A maximum width of the stiffener may be sized to be larger than a maximum width of the accompanying prosthetic material in some embodiments. And the maximum width of the stiffener may be positioned to correspond in position with the maximum width of the prosthetic material.

For purposes herein, a described shape does not require the shape to perfectly adhere to the mathematical definition of the shape. For example, a rectangular shape may have rounded corners and still be considered to have a rectangular shape.

For purposes herein, the term "flat" does not require an element to be perfectly planar. For example, a stiffener having a width and height of twenty centimeters and a thickness of one centimeter would be considered flat even if the surfaces were to have small protuberances, depressions, cutouts, and/or the stiffener were to be slightly curved out of plane. A flat carrier, flat stiffener, and a flat prosthetic material are each considered flat if their length and width dimensions are significantly larger than their thickness dimension.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements, i.e., elements that are conjunctively present in some cases and disjunctively present in other cases. Multiple elements listed with "and/or" should be construed in the same fashion. i.e., "one or more" of the elements so conjoined. Other elements may optionally be present other than the elements specifically identified by the "and/or" clause, whether related or unrelated to those elements specifically identified.

The use of "including." "comprising." "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the invention recited in the claims appended hereto.

What is claimed is:

1. A surgical material assembly comprising:
a flexible carrier including a first surface and an opposed second surface;
a hernia repair prosthetic material held within the carrier between the first and second surfaces, the hernia repair prosthetic material having a first side and a second side; and
a stiffener positioned within the carrier adjacent to the hernia repair prosthetic material, the stiffener being positioned on only the first side of the hernia repair prosthetic material, and the stiffener being stiffer than the carrier in resisting out of plane bending, wherein the stiffener has a shape that includes a transverse portion and at least one portion extending away from the transverse portion, wherein at least one opening is provided through the stiffener between the transverse portion and the at least one portion extending away from the transverse portion.

2. A surgical material assembly as in claim 1, wherein:
the transverse portion and the at least one portion extending away from the transverse portion define an X-shape, an I-shape, or a T-shape.

3. A surgical material assembly as in claim 2, wherein the at least one portion extending away from the transverse portion extends at a diagonal from the transverse portion.

4. A surgical material assembly as in claim 1, wherein the at least one portion extending away from the transverse portion extends perpendicularly from the transverse portion.

5. A surgical material assembly as in claim 1, wherein the stiffener includes a projecting portion that defines a handle.

6. A surgical material assembly as in claim 5, wherein the projecting portion has an arcuate shape.

7. A surgical material assembly as in claim 6, wherein the handle is integral with the transverse portion.

8. A surgical material assembly as in claim 1, wherein the at least one opening includes an opening on a first side of the portion extending away from the transverse portion, and an opening on a side of the portion extending away from the transverse portion opposite of the first side.

9. A surgical material assembly as in claim 1, wherein the portion extending away from the transverse portion includes a first portion and a second portion, wherein the first portion and the second portion intersect, and wherein the at least one opening is located between the intersecting first portion and second portion.

10. A surgical material assembly as in claim 1, wherein the portion extending away from the transverse portion has a T-shape or an X-shape.

11. A surgical material assembly as in claim 1, wherein the at least one opening has a triangular shape.

* * * * *